United States Patent [19]

Eisenbeis et al.

[11] Patent Number: 5,492,813
[45] Date of Patent: Feb. 20, 1996

[54] MUTEINS OF β-GALACTOSIDASE FRAGMENTS HAVING INCREASED ACTIVITY

[75] Inventors: Scott J. Eisenbeis; Sophie J. Boguslawski, both of Indianapolis, Ind.; Mark Krevolin, Pinole, Calif.; David J. Ledden, Indianapolis, Ind.

[73] Assignee: Boehringer Mannheim Corporation, Indianapolis, Ind.

[21] Appl. No.: 146,673

[22] Filed: Nov. 1, 1993

[51] Int. Cl.⁶ .............................. C12N 9/38; C12N 15/56; G01N 33/535
[52] U.S. Cl. ............................ 435/7.6; 435/18; 435/69.1; 435/172.1; 435/188; 435/207; 435/963; 930/240; 935/14
[58] Field of Search ............................ 435/7.6, 18, 69.1, 435/172.1, 207, 963, 188; 930/240; 935/14

[56] References Cited

U.S. PATENT DOCUMENTS 5,120,653 6/1992 Henderson .......................... 435/252.33

*Primary Examiner*—David Saunders
*Attorney, Agent, or Firm*—Marilyn L. Amick; Max J. Kenemore; D. Michael Young

[57] ABSTRACT

Muteins of enzyme acceptor polypeptide fragments of β-galactosidase are provided which exhibit substantially increased kinetic complementation activity with no significant loss in stability. A preferred enzyme acceptor fragment has an amino acid other than cysteine located at position 500 of the natural sequence. An especially preferred substitution is serine or valine. Other preferred muteins have an amino acid other than methionine located at position 443, with leucine being especially preferred, or an amino acid other than cysteine at position 76, with leucine being an especially preferred substitution. Also provided are methods for producing the novel muteins, reagent compositions comprising the novel muteins, and immunoassay methods for determining an analyte in which the novel mutein recombines with an enzyme donor polypeptide fragment to form enzymatically active β-galactosidase.

36 Claims, 4 Drawing Sheets

MUTEINS OF β-GALACTOSIDASE FRAGMENTS HAVING INCREASED ACTIVITY

BACKGROUND

The present invention relates to modified enzyme acceptor polypeptide fragments of β-galactosidase which have increased activity, to processes for the preparation thereof, and to the use thereof as reagents in enzyme complementation immunoassays.

A number of homogeneous immunoassays have recently been described that utilize the complementation or reassociation of enzymatically-inactive polypeptide fragments to form active enzymes as a step of generating a detectable signal which can be utilized to determine the amount of an analyte of interest that may be present in a sample such as blood serum. Several of these assays propose utilizing the enzyme β-galactosidase as the enzyme formed by complementation.

Enzyme complementation involves the association of two or more inactive polypeptides which together provide the structural information required for the formation of a biologically active enzyme complex resembling that of the native parent enzyme. The enzymatically-inactive polypeptide fragments can be obtained as the result of proteolysis, chemical cleavage, chemical synthesis, or as the result of a missense or nonsense mutation of the gene coding for the active enzyme. Examples of protein complementation systems which yield an enzymatically-active complex are the ribonuclease-S' complex, the staphylococcal nuclease T complex, various two- and three-fragment complexes derived from cytochrome c, and the alpha- and omega-complementation complexes of *E. coli* β-galactosidase. The interactions which stabilize these complexes are non-covalent in nature and are similar to those involved in the formation and maintenance of the three-dimensional structure of the native enzyme.

Enzyme complementation has been utilized as the underlying basis for the development of a novel homogeneous immunoassay technology. Farina and Golke, U.S. Pat. No. 4,378,428 issued Mar. 29, 1983, and Gonelli et al., (1981, *Biochem. and Biophys. Res. Commun.* 102:917–923) describe an immunoassay based upon the reassociation of S-peptide and S-protein, both of which are derived from the proteolytic cleavage of ribonuclease A, to generate ribonuclease catalytic activity. Specific components of the assay system include an analyte covalently attached to the S-peptide (amino acids 1–20), free S-protein (amino acids 21–124), an antibody specific for the analyte, and a substrate of ribonuclease which is capable of being converted to a reporter molecule. The anti-analyte antibody inhibits the association of the analyte:S-peptide conjugate with the S-protein, thereby reducing the level of enzymatically-active complex and thus the signal generated by the enzymatic reaction. In the presence of a sample containing free analyte, a competition for the antigen binding site occurs between sample-born analyte and the S-peptide conjugate. The concentration of S-peptide conjugate free to participate in complementation with the S-protein fragment, and the resulting signal due to the enzymatic activity of the ribonuclease A' complex, are directly proportional to the concentration of free analyte in the sample.

A similar immunoassay system based on the alpha-complementation system of *E. coli* β-galactosidase polypeptide fragments is described in Henderson, U.S. Pat. No. 4,708,929, issued Nov. 24, 1987, and Henderson, PCT Appl. No. PCT/US90/02491, published Nov. 15, 1990, both of which are incorporated herein by reference. β-Galactosidase alpha-complementation involves the association of an alpha-acceptor polypeptide fragment and an alpha-donor polypeptide fragment and the subsequent formation of an enzymatically active β-galactosidase molecule. The alpha-acceptor is derived from the internal deletion or chain interruption of consecutive amino acids located within the N-terminus proximal segment of the β-galactosidase molecule. Specific examples include the lac Z M15 β-galactosidase deletion mutant lacking residues 11–41 of the wild-type sequence, and the lac Z M112 mutant in which residues 23–31 have been deleted. The alpha-donor polypeptide can be derived from chemical or proteolytic cleavage of the wild-type protein. The cyanogen bromide fragment CNBr2 composed of amino acid residues 3–92, or the V8 protease peptide spanning residues 3–40, both possess alpha-donor activity.

Alpha-donor and alpha-acceptor polypeptides can also be generated through the application of recombinant DNA technology and peptide synthesis techniques. A readily available supply of these molecules and the ability to modify the structure of either the alpha-donor or the alpha-acceptor polypeptides through these techniques has led to the development of an optimized complementation system which has been employed in cloned enzyme donor-based homogeneous immunoassays. The alpha-donor molecule can be chemically coupled with a specific analyte of interest through the modification of either a cysteine or lysine residue which has been suitably located within the sequence of the alpha-donor molecule such that the conjugation does not interfere with the complementation reaction. Complementation between the alpha-acceptor and alpha-donor can be modulated by an antigen-antibody reaction between an analyte-specific antibody and the alpha-donor to which an analyte has been conjugated. In the presence of free analyte, a competition between the free and alpha-donor-conjugated analyte is established for the antigen binding site of the antibody. Thus, an increase in the level of free analyte results in an elevation in the quantity of alpha-donor conjugate which is available for complementation with alpha-acceptor. As a result, the concentration of the alpha-acceptor:alpha-donor complex and reporter molecule produced from the reconstituted enzymatic activity increase and are proportional to the concentration of the free analyte present in the sample. A dose response curve can be constructed by following the activity, i.e., the slope of the rate of the reaction, at several different concentrations of free analyte. The enzyme activity observed at an infinite concentration of free analyte or in the absence of antibody is defined as the "open rate" and represents the maximal signal obtainable from the assay system.

Krevolin and Kates, European Appl. No. 92304354.1, published Nov. 19, 1992, the content of which is herein incorporated by reference, describe enzyme complementation assays involving complementation in the omega region of β-galactosidase between two polypeptide fragments of the whole β-galactosidase molecule formed by a break in the primary structure of β-galactosidase in the omega region. As in alpha complementation, in some cases the two fragments are not strictly complementary so as to form an exact β-galactosidase amino acid sequence without gaps or overlaps; both gaps and overlaps are possible as long as the resulting fragments can assemble into an active β-galactosidase molecule. Like the alpha-acceptor, the omega-acceptor polypeptide is the larger of the two fragments and normally contains about two-thirds of the amino acid sequence of the natural or modified, full-length β-galactosidase. The omega-donor molecule is the smaller fragment containing the remaining one-third (approximately) of the amino acid sequence; the omega-donor molecule is derived from the C-terminus of the β-galactosidase molecule.

β-Galactosidase is a tetrameric protein having a molecular weight of about 540,000 daltons. The four identical monomers consist of 1023 amino acids, each with a molecular weight of 116,000 daltons. The monomeric protein is divided into three regions: the N-terminus proximal segment (the alpha region), a middle region, and a C-terminus distal segment (the omega region).

E. coli β-galactosidase is derived from the Z gene of the lac operon and catalyzes the hydrolysis of β-D-galactopyranosides. The catalytic mechanism of this enzyme involves the general acid catalysis of the glycosidic ester linkage of a substrate molecule by tyrosine-503. This is followed by the loss of the aglycon moiety and the stabilization of a putative carbonium ion intermediate through an interaction with glutamate-461. The final step in the catalytic cycle involves the transgalactosylation of an acceptor molecule, usually water, and the removal of the product from the active site. The active enzyme is composed of four identical subunits with one active site per subunit. Monovalent cations, although not required for activity, dramatically enhance the rate of enzyme catalysis, whereas divalent cations, e.g., $Mg^{2+}$ or $Mn^{2+}$, are required for activity.

The E. coli β-galactosidase homotetramer contains 64 cysteine residues (16 cysteine residues per subunit), none of which are involved in either the enzymatic activity or the maintenance of the quaternary structure through intersubunit disulfide bridges, as indicated by the stabilization of the molecule in high concentrations of reducing agents. The efficiency of the in vitro association of individual monomers to form the active tetramer is dramatically increased under conditions in which the cysteines are fully reduced. Similarly, reducing agents greatly enhance enzyme complementation. The alpha-acceptor polypeptide contains all 16 cysteine residues present in a single β-galactosidase subunit. However, alpha-acceptor molecules exist as homodimers in solution. Thus, the surface area normally buried at the dimer-dimer interface in β-galactosidase is exposed in the alpha-acceptor. Chemical modification studies of β-galactosidase with iodoacetate lead to the identification of cysteine-500 and cysteine-1021 as surface accessible residues in β-galactosidase (Jornvall et al., 1978, Biochem. 17, 5160–64). Carboxymethylation of these two residues did not affect the activity of the enzyme to any significant extent. However, when M15, a dimeric alpha-acceptor molecule, was treated with iodoacetate, three additional cysteine residues at positions 76, 389 and 602 were modified. Carboxymethylation was found to inhibit the ability of M15 to participate in alpha-complementation. This suggests that one or more of these additional residues is situated at the dimer-dimer interface, the modification of which interferes with alpha-complementation.

In the present invention, it has been discovered, quite unexpectedly, that modification of certain of the amino acid residues resulted in a significant increase in activity of the enzyme. This increase in activity occurred not only with respect to the complementation activity, which is the rate at which the catalytically-inactive donor and acceptor dimers combine to form the catalytically-active β-galactosidase tetramer, but also with respect to the equilibrium activity, or the rate at which the reformed β-galactosidase tetramer converts a substrate. By increasing β-galactosidase activity, the sensitivity of an assay for an analyte is increased, and such increase in sensitivity means that certain analytes which are present in blood serum in very minute quantities, such as drugs and drug metabolites, can be detected more accurately. Using the muteins of the present invention, the sensitivity of an assay can be increased as much as 1.3- to 3-fold or greater without a significant loss of enzyme stability.

Predetermined, site-directed mutagenesis of tRNA synthetase in which a cysteine residue is converted to serine has been reported (G. Winter et al., 1982, Nature, 299, 756–758, and A. Wilkinson et al., 1984, Nature, 307, 187–188). Estell et al., U.S. Pat. No. 4,760,025, issued Jul. 26, 1988 describe a cloned subtilisin gene modified at specific sites to cause amino acid substitutions of certain methionine residues. Koths et al., U.S. Pat. No. 4,752,585 issued Jun. 21, 1988 and U.S. Pat. No. 5,116,943, issued May 26, 1992, describe the protection of a therapeutic protein such as interleukin-2 or interferon-β against oxidation by substituting a conservative amino acid for each methionyl residue susceptible to chloramine T or peroxide oxidation.

Buchwalter et al., European Appl. No. 91106224.8, published Nov. 27, 1991, describe an animal somatotropin derivative in which cysteine has been substituted by site-specific mutagenesis techniques for certain serine and tyrosine residues and in which glutamic acid has been substituted for certain cysteine residues. Breddam et al., PCT/DK91/00103 published Oct. 31, 1991, describe chemically modified detergent enzymes wherein one or more methionines have been mutated into cysteines, and then said cysteines are subsequently chemically modified in order to improve stability of the enzyme toward oxidative agents. Mattes et el., U.S. Pat. No. 4,963,469, issued Oct. 16, 1990, describe a change of an amino acid in the region between amino acid 430 and 550 of β-galactosidase to another amino acid to produce an enzymatically inactive, immunologically active β-galactosidase mutein. Estell et al. (1985, J. Biol. Chem. 260, 6518–6521) used site-directed mutagenesis to alter the methionine 222 residue of subtilisin which is a primary site for oxidative inactivation of the enzyme. These authors found that mutants containing non-oxidizable amino acids, i.e., serine, alanine and leucine, were resistant to peroxide inactivation, whereas methionine and cysteine-substituted enzymes were rapidly inactivated.

In copending and commonly assigned application U.S. Ser. No. 08/146,633 filed Oct. 29, 1993, the content of which is herein incorporated by reference, it was discovered that substitution by site-directed mutagenesis of the cysteine-602 residue on an enzyme acceptor polypeptide fragment of β-galactosidase with a conservative amino acid, preferably serine, results in substantially increased stability of the enzyme acceptor mutein over that of an enzyme acceptor polypeptide fragment having cysteine at position 602.

As used herein, the numbering for the amino acid residues of β-galactosidase will be that published by Kalnins et al., 1983, EMBO Journal 2, 593–597, the content of which is herein incorporated by reference. The nucleotide sequence of the lac Z gene coding for β-galactosidase in E. coli was determined and β-galactosidase was predicted to consist of 1023 amino acid residues rather than the 1021 residues previously reported by Fowler and Zabin (1977, Proc. Natl. Acad. Sci. USA 74, 1507–1510 and 1978, J. Biol. Chem. 253, 5521–5525).

SUMMARY OF THE INVENTION

The present invention provides novel muteins of enzyme acceptor polypeptide fragments of β-galactosidase and processes for producing such muteins. In particular, the present invention provides novel enzyme acceptor fragments having an amino acid substitution at at least one of the following sites: cysteine-500, methionine-443 and cysteine-76. In one embodiment of the present invention, there are provided novel muteins of enzyme acceptor polypeptide fragments of β-galactosidase in which an amino acid other than cysteine is located at position 500. Especially preferred are alpha-acceptor polypeptide fragments of β-galactosidase in which serine or valine is substituted for cysteine-500.

In another embodiment, the present invention also provides novel muteins of enzyme acceptor polypeptide fragments of β-galactosidase in which an amino acid other than methionine is located at position 443. Particularly preferred are alpha-acceptor polypeptide fragments of β-galactosidase in which leucine is substituted for methionine-443.

In yet another embodiment, the present invention also provides novel muteins of enzyme acceptor polypeptide fragments of β-galactosidase in which an amino acid other than cysteine is located at position 76. Particularly preferred are alpha-acceptor polypeptide fragments of β-galactosidase in which leucine is substituted for methionine-443.

Muteins having more than one substitution are also provided by the present invention; however, at least one of the substitutions must be at amino acid position 500, 443 or 76.

The novel muteins of the present invention have been found to have significantly increased activity, both complementation as well as catalytic activity. Although there is no significant decrease in stability of the muteins of the present invention or reagent compositions comprising the muteins, random mutagenesis at any of these sites could produce a mutein with both enhanced activity and stability.

Further provided are reagent compositions comprising these novel muteins and immunoassay methods utilizing such compositions in cloned enzyme donor immunoassays involving complementation between these enzymatically-inactive donor and acceptor fragments to form an enzymatically-active enzyme. The novel enzyme acceptor muteins of the present invention have been found to exhibit substantially increased equilibrium and kinetic complementation activity over that of the parent enzyme acceptor fragment.

The novel muteins of the present invention are conveniently prepared by causing site-directed mutagenesis at the appropriate location on the gene coding for the parent enzyme acceptor. Site-directed mutagenesis methods (Wallace et al., 1981, *Nucleic Acids Res.* 9, 3647–3656; Zoller and Smith, 1982, *Nucleic Acids Res.* 10, 6487–6500; and Deng and Nickoloff, 1992, *Anal. Biochem.* 200, 81–88) permit the replacement of cysteine- 500, methionine-443 or cysteine-76 of β-galactosidase with any amino acid. Chemical synthesis of the polypeptide fragment is not beyond the scope of the present invention; however, such techniques are generally applied to the preparation of polypeptides that are relatively short in amino acid length.

In an assay according to the present invention, an analyte in a sample such as blood serum, i.e., a ligand or receptor, is determined using reagent compositions comprising enzyme donor and enzyme acceptor polypeptide fragments, wherein the enzyme donor fragment is conjugated to an analyte-binding protein specific for the analyte, and wherein the analyte is cross-reactive with the conjugated analyte-binding protein or is complementary thereto. The enzyme acceptor polypeptide consists essentially of a fragment of β-galactosidase which is characterized by forming with the enzyme donor an active enzyme complex having β-galactosidase activity in the absence of analyte-binding protein binding to said conjugate. The reagents are combined with the sample and a substrate capable of reacting with the active enzyme complex in an appropriate assay medium. The rate of conversion of the substrate by the enzyme compared to the rate of conversion of substrate obtained using a known concentration of the analyte is used to determine the amount of analyte in the sample.

BRIEF DESCRIPTION OF THE DRAWINGS

The present invention will be better understood by reference to the following detailed description of the invention when considered in combination with the drawings that form part of the specification, wherein.

DESCRIPTION OF SPECIFIC EMBODIMENTS

Figure 1:
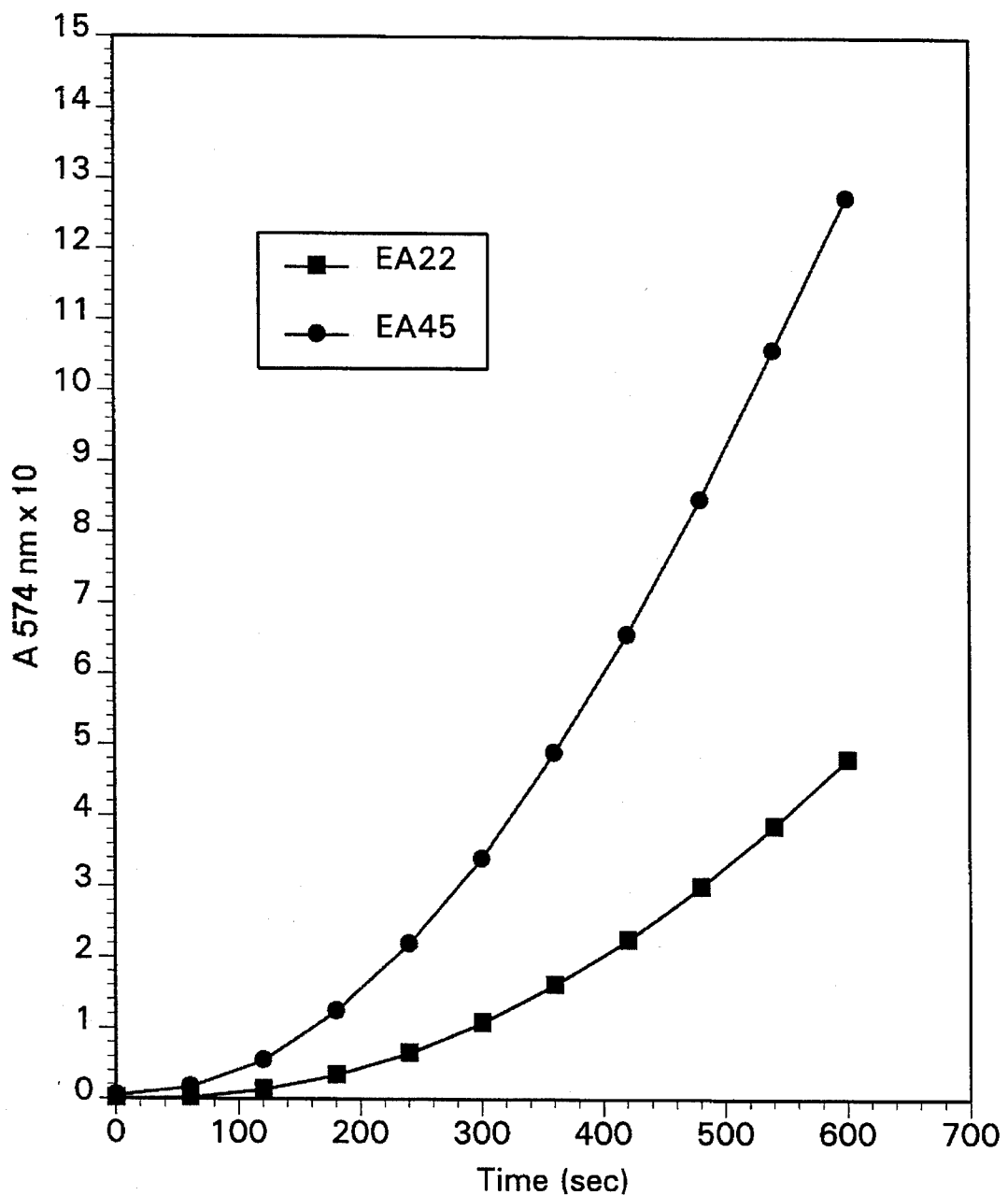
FIG. 1 is a graph comparing the kinetic β-galactosidase activity of the mutein EA45 of the present invention with the kinetic activity of the parent enzyme acceptor, EA22.

In accordance with the present invention, the novel enzyme acceptor polypeptide fragments of β-galactosidase are prepared by site-directed mutagenesis methods, wherein a particular location on the gene coding for an enzyme acceptor fragment is mutagenized. In one embodiment of the present invention, site-directed mutagenesis methods are used to cause a mutation at the location coding for cysteine at position 500 in the natural sequence, thereby causing the substitution of a conservative amino acid for cysteine. A preferred amino acid substitution is valine or serine. Other amino acids may also be substituted, but conservative substitutions are preferred. By conservative substitution is meant replacement of an amino acid of β-galactosidase by an amino acid which has similar characteristics and which is not likely to have an adverse effect on either the enzyme acceptor's ability to complement with enzyme donor or on the catalytic activity of the reformed β-galactosidase. Examples of such conservative amino acid substitutions are glycine, alanine, valine, leucine, isoleucine, serine, threonine and methionine. An especially preferred substitution for cysteine is serine or valine, and an especially preferred parent enzyme acceptor is EA22, which is described fully in U.S. Pat. No. 4,708,929.

In another embodiment of the present invention, site-directed mutagenesis methods are used to cause a mutation at the location coding for methionine at position 443 in the natural sequence, thereby causing the substitution of a conservative amino acid for methionine. An especially preferred amino acid substitution is leucine.

In yet another embodiment of the present invention, site-directed mutagenesis methods are used to cause a mutation at the location coding for cysteine at position 76 in the natural sequence, thereby causing the substitution of a conservative amino acid for cysteine. A preferred amino acid substitution is leucine or serine. Other amino acids may also be substituted, but conservative substitutions are preferred.

The preparation of parent enzyme acceptors can be accomplished using a variety of recombinant DNA techniques, including deletion constructions or direct synthesis of DNA carrying the desired amino acid sequence followed by in frame ligation into the DNA sequence of the alpha-region of the lac Z gene which encodes native β-galactosidase. Such techniques are described more fully in U.S. Pat. No. 4,708,929.

Organisms producing parent enzyme acceptor polypeptide fragments are also publicly available. E. coli strain AMA 1004, In Vitro International, Inc. (IVI) (Ann Arbor, Mich.), accession no. 10051, contains a plasmid, pMG22, which carries a gene for a β-galactosidase enzyme acceptor with amino acids 13–40 deleted (EA22). E. coli strain AMA 1004, IVI 10050, contains a plasmid, pMG14, which carries a gene for a β-galactosidase enzyme acceptor with amino acids 30–37 deleted (EA14).

As defined herein, an enzyme acceptor is an enzymatically-inactive polypeptide produced by a deletion mutant of the β-galactosidase gene which, when combined with an enzyme donor, is capable of forming enzymatically-active β-galactosidase by the process of complementation. The particular substituted enzyme acceptor muteins described herein are produced from EA22, an enzyme acceptor having a deletion within the alpha-region of the β-galactosidase gene encoding the N-terminus of the β-galactosidase protein. Specifically, EA22 has a deletion of amino acid residues 13–40. Other enzyme acceptor fragments of β-galactosidase which contain the natural sequence which includes amino acid position 602 may also be used to produce muteins according to the present invention. Specific examples of enzyme alpha-acceptors are disclosed in U.S. Pat. No. 4,708,929 and include EA5, EA11, EA14, EA17, EA18, EA20, EA23 and EA24. The distal end of the deletion segment in suitable alpha-acceptors will normally fall between amino acid positions 26 and 54 of the β-galactosidase sequence. In EA22, the distal end of the deletion segment is amino acid 40.

Although alpha-acceptor fragments are exemplified herein, omega-acceptor fragments are also within the scope of the present invention. Omega-acceptors are fully described in European Appl. 92304354.1, and a specific example of a suitable parent omega-acceptor is OA721.

The chief consideration when selecting an enzyme acceptor polypeptide of β-galactosidase for modification according to the teachings of the present invention is that there has been no previous deletion at the position where the desired mutagenesis is to take place, i.e., either amino acid 500, 443 or 76 as appropriate.

As defined herein, an enzyme donor is an enzymatically inactive polypeptide comprised of two domains, a donor domain containing a protein sequence capable of combining with an enzyme acceptor to form active enzyme, and an analyte domain capable of interacting with an analyte-binding protein. The analyte domain is either (a) an analyte-coupling domain through which attachment to various analytes or analyte analogs can be accomplished or (b) a protein domain which itself functions as an analyte analog. An especially preferred enzyme donor, ED4, is described in detail in U.S. Pat. No. 4,708,929.

In the assay method of the present invention, a known amount of an enzyme donor of the β-galactosidase system comprising a coupled or fused analyte (or analogous analyte derivative) of interest, i.e., the enzyme donor conjugate, is combined with a known amount of a specific analyte-binding protein or other binding molecule and a known amount of an enzyme acceptor capable of complementation with the enzyme donor. Competition between the analyte domain of the enzyme donor conjugate and free unknown analyte in the sample for the known amount of specific analyte-binding protein allows the enzyme donor conjugate to remain free so that it binds to the enzyme acceptor. The association of donor conjugates and acceptor results in the formation of a catalytically active enzyme complex, thus modulating the amount of β-galactosidase enzyme activity detectable in the sample. As a result, the amount of free analyte in the sample is determined as a direct function of the measurable enzyme activity. Enzyme activity is measured by monitoring the rate of substrate conversion by the enzyme catalyzed reaction by any of a variety of techniques, including but not limited to spectrophotometric and fluorometric methods.

As used herein, kinetic activity includes both the rate of complementation of the enzyme acceptor with the enzyme donor as well as the catalytic activity of the reformed β-galactosidase. Equilibrium activity is the catalytic activity of the reformed β-galactosidase after complementation of the enzyme acceptor with the enzyme donor has been completed.

EXAMPLE 1

Construction of Enzyme Acceptor Mutein EA500V

Mutein EA500V was constructed by site-directed mutagenesis of the alpha-acceptor parent, EA22, according to the method of Deng and Nickoloff, supra. The starting plasmid which contained the structural gene for EA22 was p230. Two oligonucleotide primers were synthesized which contained twenty uninterrupted bases for hybridization as well as a substitution which introduced the cysteine to valine substitution at position 500. Additionally, the primers incorporated a new restriction endonuclease site and removed a native restriction endonuclease site for screening and selection purposes, respectively.

After the two primers were annealed to the denatured p230, they were elongated with DNA polymerase and transformed via electroporation into a mut S E. coli strain defective in strand repair, BMH 71–18. A pool of plasmid obtained from an overnight culture of these cells was transformed again into a lac Z deleted strain, AMA 1004. Plasmids from individual colonies were screened for introduction of a new unique restriction endonuclease site. Positive clones were sequenced for the incorporation of the cysteine-500 to valine change. The final mutagenized product was plasmid p230 with a mutagenized amino acid at the cysteine-500 position as well as two silent changes, one beside the mutagenized amino acid and one at the unique site position elsewhere on the plasmid.

EXAMPLE 2

Construction of Enzyme Acceptor Mutein EA45

Mutein EA45 was constructed by site-directed mutagenesis of the alpha-acceptor parent, EA22, according to the method of Deng and Nickoloff, supra. The starting plasmid which contained the structural gene for EA22 was p230. Two oligonucleotide primers were synthesized which contained twenty uninterrupted bases for hybridization as well as a substitution which introduced the methionine to leucine substitution at position 443. Additionally, the primers incorporated a new restriction endonuclease site and removed a native restriction endonuclease site for screening and selection purposes, respectively.

After the two primers were annealed to the denatured p230, they were elongated with DNA polymerase and transformed via electroporation into a mut S *E. coli* strain defective in strand repair, BMH 71–18. A pool of plasmid obtained from an overnight culture of these cells was transformed again into a lac Z deleted strain, AMA 1004. Plasmids from individual colonies were screened for introduction of a new unique restriction endonuclease site. Positive clones were sequenced for the incorporation of the methionine-443 to leucine change. The final mutagenized product was plasmid p230 with a mutagenized amino acid at the methionine-443 position as well as two silent changes, one beside the mutagenized amino acid and one at the unique site position elsewhere on the plasmid.

EXAMPLE 3

Construction of Enzyme Acceptor Mutein EA51

Enzyme acceptor mutein EA51 was constructed using insertion cassette mutagenesis techniques. A synthetic oligonucleotide containing the cysteine-76 to leucine change was made double-stranded enzymatically using DNA polymerase Klenow fragment and digested with restriction enzymes, allowing it to be cloned into the β-galactosidase gene at the 76 position.

EXAMPLE 4

Construction of Enzyme Acceptor Muteins EA33 and EA34

The plasmid which contains the structural gene for EA33 was derived from two starting plasmids, p22 and p204. Plasmid p22 codes for EA22, and p204 is a plasmid carrying site mutations at positions 500 and 1021.

The construction of p204 was accomplished by cutting and pasting two plasmids, p201 and p202, which carried the desired mutations. Plasmid p201, which carries the substitution of serine for cysteine-1021, was produced by an exonuclease III/priming procedure in which the starting plasmid, p200, which carries the structural gene for wild-type β-galactosidase, was linearized by cutting at a unique restriction site. The 3' strands at the cut site were chewed back by exonuclease III in a time-dependent manner, revealing various lengths of single-stranded DNA. After the mutagenic site was made single-stranded, the primer DNA was added and hybridized to the single-stranded template. This was elongated using DNA polymerase Klenow fragment, T4 DNA ligase and DNA polynucleotide kinase and transformed into AMA 1004. The correct mutant was detected by a restriction site variation inserted with the mutagenic primer. Plasmids p201 and p202 were combined using standard gene splicing techniques. The EA22 deletion was then transferred into p204 by gene splicing to produce p211, which codes for EA33.

To make EA34, the 76 mutagenic site, produced by the exonuclease III procedure, was spliced into p211 to produce p212, which codes for EA34.

EXAMPLE 5

Comparison of Kinetic and Equilibrium Activities

Several comparison studies were made in which the kinetic and the equilibrium activities of the enzyme acceptor muteins were measured. Since the experiments were not all done at the same time under the same conditions, the results obtained are expressed in the table below as a percentage of EA22 activity for purposes of comparison as a group.

| Mutein | Mutation | Equilibrium Activity (% of EA22) | Kinetic Activity (% of EA22) |
|---|---|---|---|
| EA22 | parent EA | 100 | 100 |
| EA33 | cys 500 → ser<br>cys 1021 → ser | 159 | 123 |
| EA34 | cys 76 → ser<br>cys 500 → ser<br>cys 1021 → ser | 169 | 135 |
| EA500V | cys 500 → val | 140 | 138 |
| EA51 | cys 76 → leu | 133 | 134 |
| EA45 | met 443 → leu | 117 | 323 |

Experiment 1 (EA22, EA33, EA34)

To measure kinetic activity, 5 µg of the appropriate enzyme acceptor and 0.6 µg of ED4 were added to an enzyme assay buffer composed of 50 mM sodium phosphate, 100 mM sodium chloride, 2 mM EDTA, 2 mM EGTA, 5 mM magnesium acetate, 3 mM ONPG (o-nitrophenyl-β-D-galactopyranoside), and 0.03% TWEEN-20 (registered TM of ICI Americas, Inc. for polyoxyethylenesorbitan), pH 7.0 at 25° C., and the reaction was monitored at 405 nm. The average ΔA/min over 15 minute reaction was used as a measure of activity. 1 unit=average ΔA/min×1000.

To measure equilibrium activity, the appropriate enzyme acceptor and ED4 at a final concentration of 4.4 µM (0.5 mg/ml) and 8.8 µM, respectively, were incubated in 0.1 ml volume at room temperature for 24 hours. 25 µl aliquots of dilutions corresponding to 10 µg/ml EA were used to measure β-galactosidase activity at 25° C. by adding to activity assay buffer. 1 unit of activity=average ΔA/min×1000.

Experiment 2 (EA22, EA51, EA500V)

Measurement of kinetic activity was performed as in Experiment 1 except that 3.75 µg EA and 0.45 µg ED4 were used per assay. To measure equilibrium activity, EA concentration was 0.22 mg/ml (1.96 µM) and ED4 was 3.67 µM in total volume of 0.09 ml. For the assay, 20 µl of dilutions corresponding to 8.8 µg/ml EA were used.

Experiment 3 (EA22, EA45)

Measurement of kinetic activity was performed as in Experiment 1 except that the reaction was monitored for 10 minutes. To measure equilibrium activity, EA concentration was 1 mg/ml (8.8 µM) and ED4 was 35.2 µM in total volume of 0.1 ml. Incubations were done at room temperature for 6 hours. For the assay, 20 µl of dilutions corresponding to 5 µg/ml EA were used.

EXAMPLE 6

Measurement of Kinetics of Complementation

The kinetic activity of β-galactosidase enzyme reformed from EA45 was compared to that of the "wild-type" parent, EA22, using enzyme donor ED4.

An activity assay buffer was prepared having the following composition:

50 mM Na phosphate, pH 7.0
100 mM NaCl
5 mM Mg acetate
2 mM ethylene glycol tetraacetic acid (EGTA)
2 mM EDTA
0.03% TWEEN-20
1 mg/ml CPRG (chlorphenylred-β-D-galactopyranoside)

Measurement of kinetic β-galactosidase activity was accomplished using 300 nM of the appropriate enzyme acceptor in assay buffer with 0.3 nM alpha-donor ED4 in the presence of the β-galactosidase chromogenic substrate CPRG in a total volume of 1.0 ml. The rate of the subsequent enzyme activity was then measured spectrophotometrically by monitoring the absorbance at 574 nm over a 10-minute period of time at 25° C. The results obtained are plotted in FIG. 1.

EXAMPLE 7

Measurement of Equilibrium Activity

The equilibrium activity of β-galactosidase enzyme reformed from EA45 was compared to that reformed from the "wild-type" parent, EA22, using enzyme donor ED4.

Figure 2:
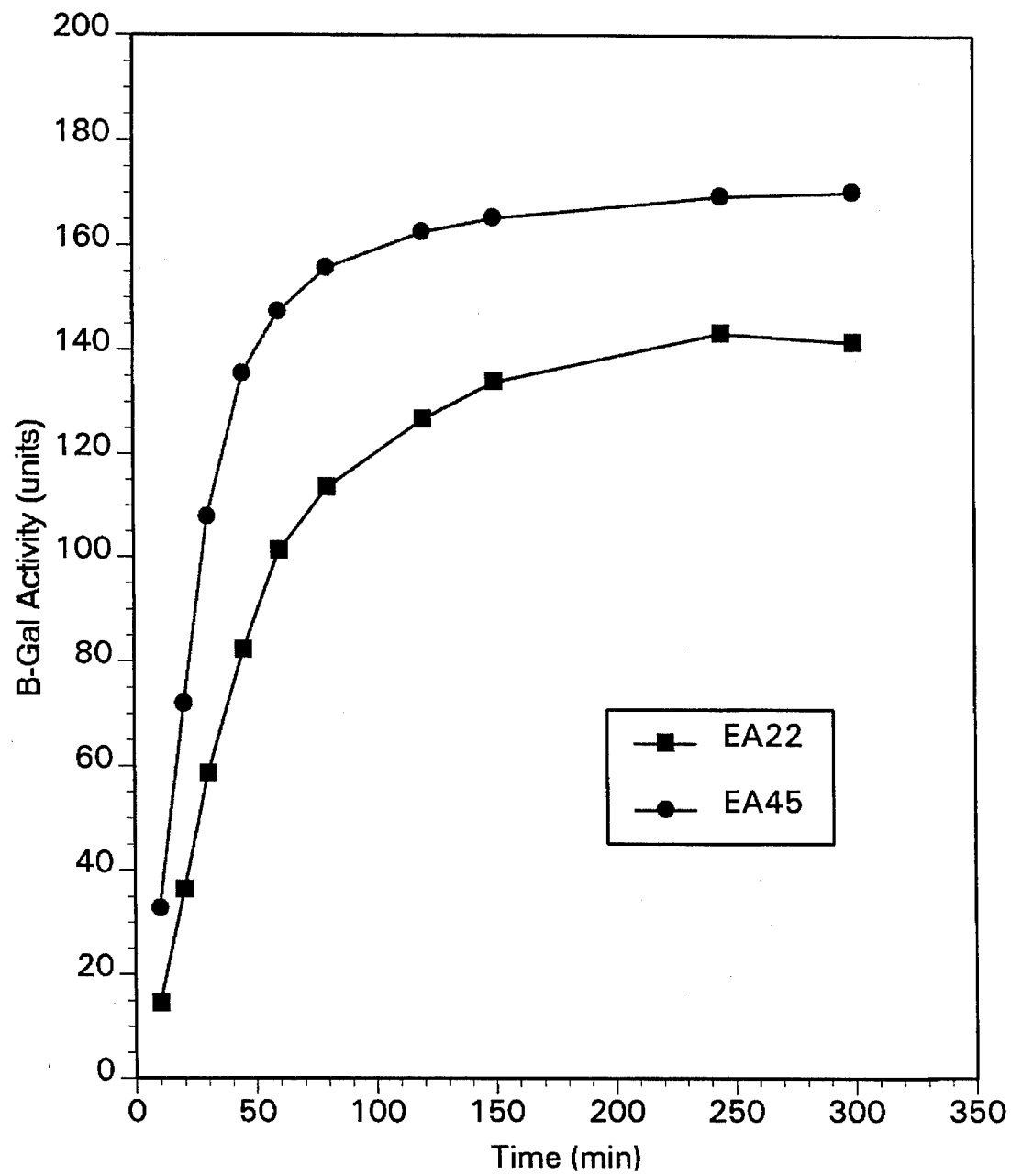
FIG. 2 is a graph comparing the equilibrium β-galactosidase activity of the mutein EA45 of the present invention with the equilibrium activity of the parent enzyme acceptor, EA22.

An activity assay buffer was prepared having the following composition:

50 mM Na phosphate, pH 7.0
100 mM NaCl
5 mM Mg acetate
2 mM EGTA
2 mM EDTA
0.03% TWEEN-20
3 mM ONPG Measurement of equilibrium activity was accomplished by incubating 0.1 μM of the appropriate enzyme acceptor and 0.2 μM alpha-donor ED4 in a buffer composed of 60 mM potassium phosphate, 400 mM sodium chloride, 10 mM EGTA, 2 mM magnesium acetate, 20 mM sodium azide, 0.05% TWEEN- 20, pH 6.9. At indicated time points, 20 μl of the incubation mixture was added to 980 μl of assay buffer. The level of the subsequent enzyme activity was then measured spectrophotometrically by measuring the rate of change in absorbance at 405 nm. The results obtained in change in absorbance/minute×1000 are plotted in FIG. 2.

EXAMPLE 8

Comparison of Equilibrium Activity

The equilibrium activity of EA33, EA34, EA51 and EA500V were compared to that of the "wild-type" parent, EA22, using enzyme donor ED4.

Figure 3:
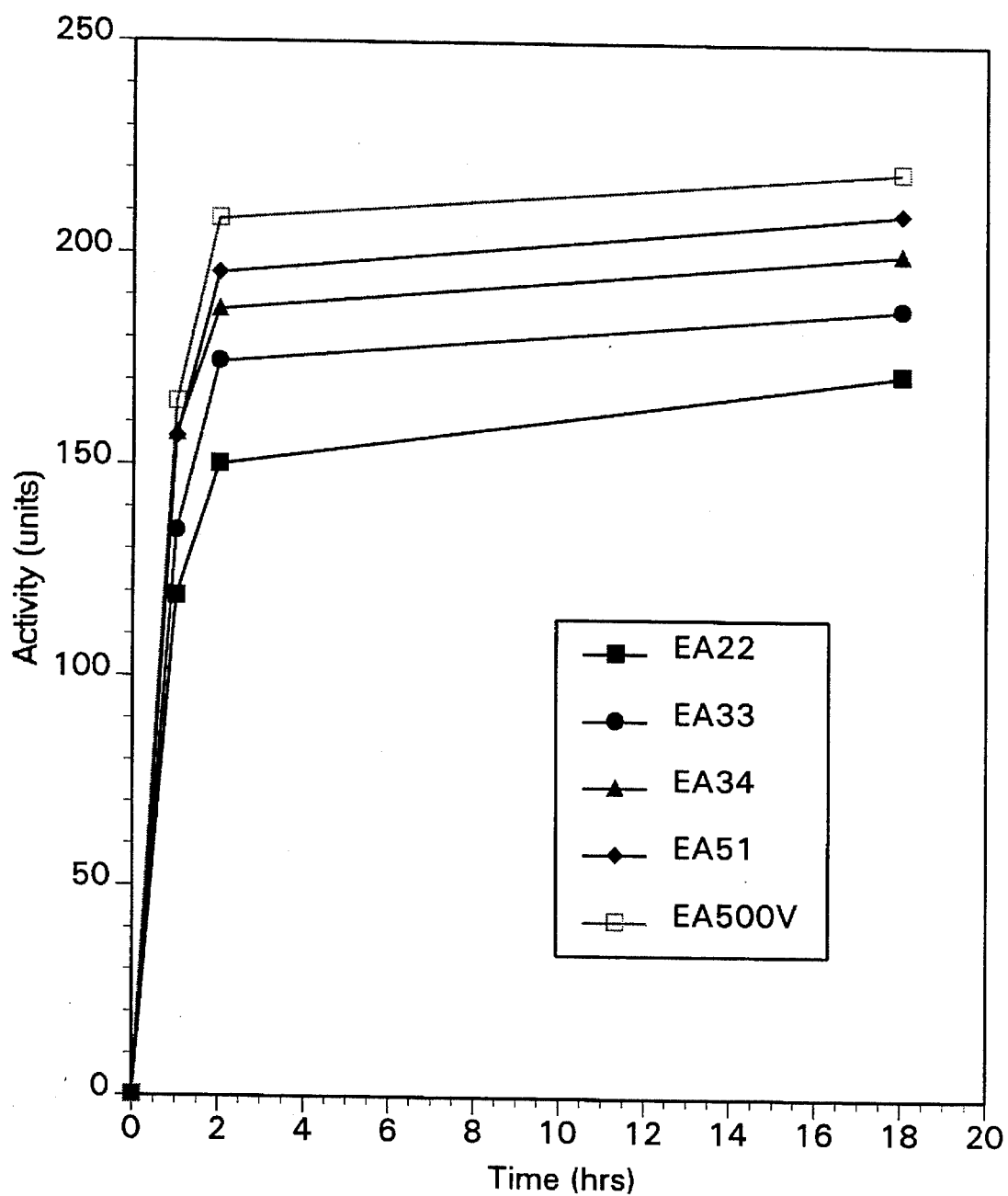
FIG. 3 is a graph comparing the equilibrium β-galactosidase activity of the muteins EA33, EA34, EA51 and EA500V of the present invention with the equilibrium activity of the parent enzyme acceptor, EA22.

An activity assay buffer was prepared having the following composition:

50 mM Na phosphate, pH 7.0
100 mM sodium chloride
5 mM Mg acetate
2 mM EGTA
2 mM EDTA
0.03% TWEEN-20
3 mM ONPG Measurement of equilibrium activities was accomplished by incubating 0.1 μM of the appropriate enzyme acceptor and 0.2 μM ED4 at room temperature in a buffer composed of 100 mM sodium phosphate, 2 mM EDTA, 2 mM EGTA, 5 mM magnesium acetate, 0.02% sodium azide, 0.03% TWEEN-20, pH 7.0. At indicated time points, 20 μl of the incubation mixture was added to 980 μl of assay buffer. The rate of the subsequent enzyme activity was then measured spectrophotometrically by measuring the rate of change in absorbance at 405 nm. The results obtained in absorbance units/minute×1000 are plotted in FIG. 3.

EXAMPLE 9

Assay for Barbiturates

Figure 4:
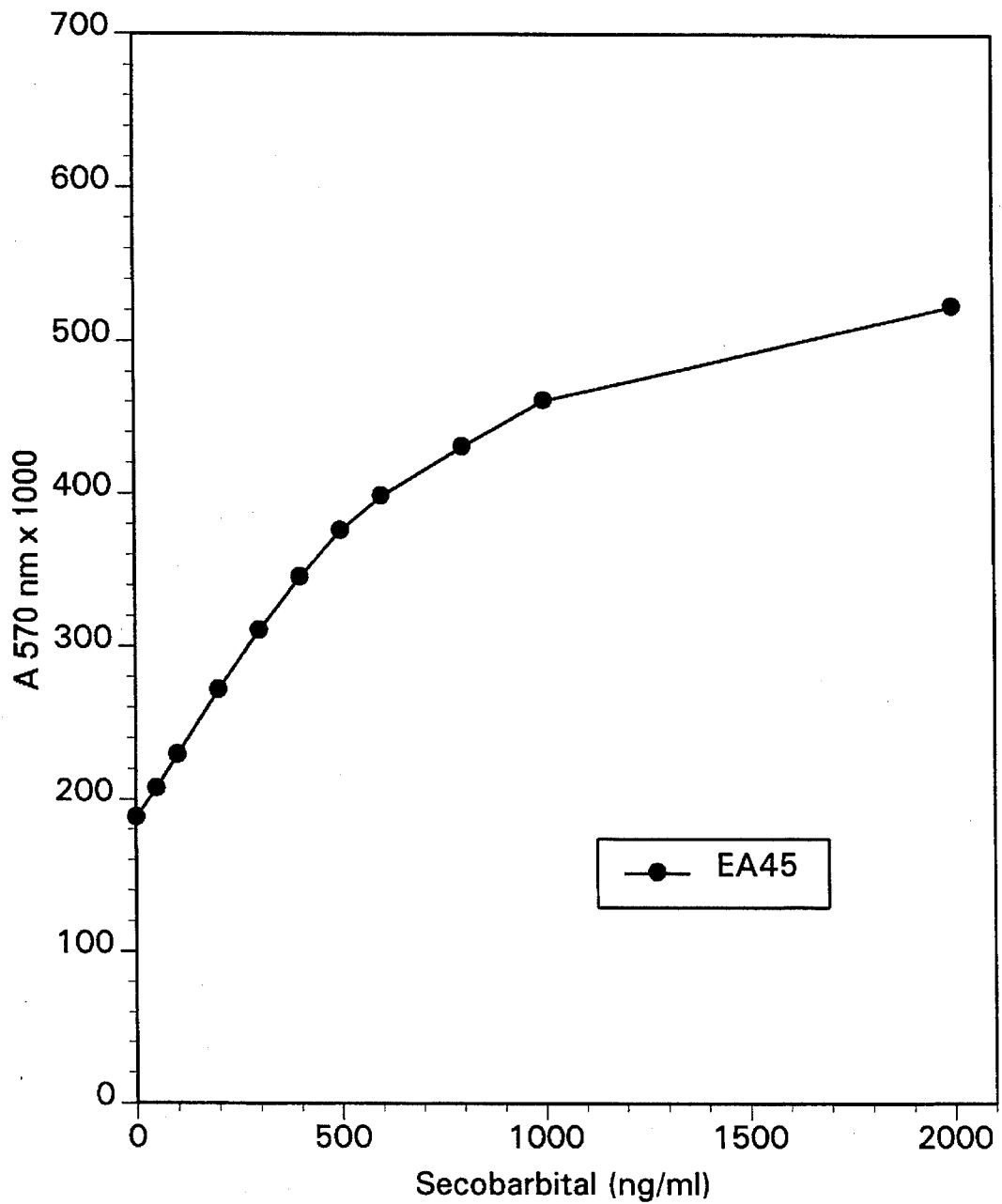
FIG. 4 is a dose response curve using mutein EA45 and showing the rate of substrate conversion by reformed β-galactosidase enzyme in response to varying levels of analyte.

In order to demonstrate the ability of EA45 to detect an analyte in a sample specimen, varying concentrations of a barbiturate dose (secobarbital) were assayed using a monoclonal antibody specific for barbiturates as the analyte-binding protein. A dose response curve was constructed for EA45 and is shown in FIG. 4.

EA Reagent
100 mM PIPES (1,4-piperazinediethanesulfonic acid), pH 6.8
600 mM NaCl
10 mM Mg Acetate
10 mM EGTA
20 mM Na Azide
0.1 mg/ml EA45
10 mM L-methionine
0.5% fetal bovine serum
1:800 dilution monoclonal barbiturate antibody (ascites)

ED Reagent
100 mM PIPES, pH 6.8
600 mM NaCl
10 mM EGTA
1 mM EDTA
20 mM Na Azide
2 mg/ml bovine serum albumin fragments
1 mg/ml CPRG
0.93 nM ED28-barbiturate conjugate Measurement of Barbiturate The assay was performed using a Hitachi 717 automated analyzer (Boehringer Mannheim Corp., Indianapolis, Ind.) using equal amounts of ED reagent and EA reagent. The secobarbital dose was added to the EA reagent and incubated for 5 minutes, following which ED reagent was added. The absorbance rate was then measured at 570 nm using a 1-minute read interval at 4'00"–5'00" following the addition of ED reagent. In this particular experiment, the reagent volumes used were 134 μl each and the sample volume was 9 μl. The doses were prepared from an Alltech Secobarbital calibrator, 10,000 ng/ml.

What is claimed is:

1. A mutein of an enzyme acceptor polypeptide of β-galactosidase having an amino acid other than cysteine substituted at position 500.

2. The mutein of claim 1, wherein said amino acid is selected from the group consisting of glycine, alanine, valine, leucine, isoleucine, serine, threonine, and methionine.

3. The mutein of claim 1, wherein said amino acid is serine or valine.

4. A mutein of an enzyme acceptor polypeptide of β-galactosidase having an amino acid other than methionine substituted at position 443.

5. The mutein of claim 4, wherein said amino acid is selected from the group consisting of glycine, alanine, valine, leucine, isoleucine, serine, and threonine.

6. The mutein of claim 4, wherein said amino acid is leucine.

7. A mutein of an enzyme acceptor polypeptide of β-galactosidase having an amino acid other than cysteine substituted at position 76.

8. The mutein of claim 7, wherein said amino acid is selected from the group consisting of glycine, alanine, valine, leucine, isoleucine, serine, threonine, and methionine.

9. The mutein of claim 7, wherein said amino acid is leucine or serine.

10. A process for producing a mutein of an enzyme acceptor polypeptide of β-galactosidase said mutein having an amino acid other than cysteine substituted at position 500, comprising providing a starting plasmid comprising a DNA sequence encoding an enzyme acceptor polypeptide of β-galactosidase, causing a site-directed mutation in the portion of said starting plasmid coding for β-galactosidase amino acid 500 which is normally cysteine, thereby forming a mutagenized plasmid, and expressing said mutagenized plasmid to produce said mutein.

11. The process of claim 10, wherein said site-directed mutagenesis comprises mutagenesis of the portion coding for cysteine at amino acid 500 to code for one selected from the group consisting of glycine, alanine, valine, leucine, isoleucine, serine, and methionine.

12. The process of claim 10, wherein said site-directed mutagenesis comprises mutagenesis of the portion coding for cysteine at amino acid 500 to code for valine or serine.

13. A process for producing a mutein of an enzyme acceptor polypeptide of β-galactosidase said mutein having an amino acid other than methionine substituted at position 443, comprising providing a starting plasmid comprising a DNA sequence encoding an enzyme acceptor polypeptide of β-galactosidase, causing a site-directed mutation in the portion of said starting plasmid coding for β-galactosidase amino acid 443 which is normally methionine, and expressing said mutagenized plasmid to produce said mutein.

14. The process of claim 13 wherein said site-directed mutagenesis comprises mutagenesis of the portion coding for cysteine at amino acid 443 to code for one selected from the group consisting of glycine, alanine, valine, leucine, isoleucine, serine and threonine.

15. The process of claim 13, wherein said site-directed mutagenesis comprises mutagenesis of the portion coding for cysteine at amino acid 443 to code for leucine.

16. A process for producing a mutein of an enzyme acceptor polypeptide of β-galactosidase, said mutein having an amino acid other than cysteine substituted at position 76, comprising providing a starting plasmid comprising a DNA sequence encoding an enzyme acceptor polypeptide of β-galactosidase, causing a site-directed mutation in the portion of said starting plasmid coding for β-galactosidase amino acid 76 which is normally cysteine, thereby forming a mutagenized plasmid, and expressing said mutagenized plasmid to produce said mutein.

17. The process of claim 16, wherein said site-directed mutagenesis comprises mutagenesis of the portion coding for cysteine at amino acid 76 to code for one selected from the group consisting of glycine, alanine, valine, leucine, isoleucine, serine, threonine, and methionine.

18. The process of claim 16, wherein said site-directed mutagenesis comprises mutagenesis of the portion coding for cysteine at amino acid 76 to code for leucine or serine.

19. A reagent composition comprising an enzyme acceptor polypeptide of β-galactosidase having an amino acid other than cysteine substituted at position 500.

20. The reagent composition of claim 19, wherein said amino acid is selected from the group consisting of glycine, alanine, valine, leucine, isoleucine, serine, threonine, and methionine.

21. The reagent composition of claim 19, wherein said amino acid is valine or serine.

22. A reagent composition comprising an enzyme acceptor polypeptide of β-galactosidase having an amino acid other than methionine substituted at position 443.

23. The reagent composition of claim 22, wherein said amino acid is selected from the group consisting of glycine, alanine, valine, leucine, isoleucine, serine and threonine.

24. The reagent composition of claim 22, wherein said amino acid is leucine.

25. A reagent composition comprising an enzyme acceptor polypeptide of β-galactosidase having an amino acid other than cysteine substituted at position 76.

26. The reagent composition of claim 25, wherein said amino acid is selected from the group consisting of glycine, alanine, valine, leucine, isoleucine, serine, threonine, and methionine.

27. The reagent composition of claim 25, wherein said amino acid is leucine or serine.

28. An immunoassay method for determining an analyte in a sample suspected of containing said analyte comprising:
  (a) contacting said sample with
    (i) an enzyme donor polypeptide conjugate,
    (ii) an analyte-binding protein specific for said analyte,
    (iii) an enzyme acceptor polypeptide of β-galactosidase wherein said enzyme acceptor polypeptide is characterized by forming with said enzyme donor polypeptide an active enzyme complex having β-galactosidase activity in the absence of analyte-binding protein binding to said conjugate, said enzyme acceptor polypeptide being further characterized by having an amino acid other than cysteine substituted at position 500, and
    (iv) a substrate capable of reacting with said active enzyme complex, such that the rate of conversion of said substrate by said active enzyme complex can be monitored, and wherein said enzyme donor conjugate is capable of competing with said analyte to bind to said analyte-binding protein, thereby inhibiting the formation of active enzyme complex;
  (b) measuring the rate of conversion of substrate; and
  (c) determining the amount of analyte in the sample by comparing the rate of conversion of substrate to a rate of conversion of substrate obtained using a known concentration of the analyte.

29. The method of claim 28, wherein said amino acid is selected from the group consisting of glycine, alanine, valine, leucine, isoleucine, serine, threonine, and methionine.

30. The method of claim 28, wherein said amino acid is serine or valine.

31. An immunoassay method for determining an analyte in a sample suspected of containing said analyte comprising:
  (a) contacting said sample with
    (i) an enzyme donor polypeptide conjugate,
    (ii) an analyte-binding protein specific for said analyte,
    (iii) an enzyme acceptor polypeptide of β-galactosidase wherein said enzyme acceptor polypeptide is characterized by forming with said enzyme donor polypeptide an active enzyme complex having β-galactosidase activity in the absence of analyte-binding protein binding to said conjugate, said enzyme acceptor polypeptide being further characterized by having an amino acid other than methionine substituted at position 443 and (iv) a substrate capable of reacting with said active enzyme complex, such that the rate of conversion of said substrate by said active enzyme complex can be monitored, and wherein said enzyme donor conjugate is capable of competing with said analyte to bind to said analyte-binding protein, thereby inhibiting the formation of active enzyme complex;

(b) measuring the rate of conversion of substrate; and (c) determining the amount of analyte in the sample by comparing the rate of conversion of substrate to a rate of conversion of substrate obtained using a known concentration of the analyte.

32. The method of claim 31, wherein said amino acid is selected from the group consisting of glycine, alanine, valine, leucine, isoleucine, serine and threonine.

33. The method of claim 31, wherein said amino acid is leucine.

34. An immunoassay method for determining an analyte in a sample suspected of containing said analyte comprising:

(a) contacting said sample with
 (i) an enzyme donor polypeptide conjugate,
 (ii) an analyte-binding protein specific for said analyte,
 (iii) an enzyme acceptor polypeptide of β-galactosidase wherein said enzyme acceptor polypeptide is characterized by forming with said enzyme donor polypeptide an active enzyme complex having β-galactosidase activity in the absence of analyte-binding protein binding to said conjugate, said enzyme acceptor polypeptide being further characterized by having an amino acid other than cysteine substituted at position 76, and (iv) a substrate capable of reacting with said active enzyme complex, such that the rate of conversion of said substrate by said active enzyme complex can be monitored, and wherein said enzyme donor conjugate is capable of competing with said analyte to bind to said analyte-binding protein, thereby inhibiting the formation of active enzyme complex;

(b) measuring the rate of conversion of substrate; and (c) determining the amount of analyte in the sample by comparing the rate of conversion of substrate to a rate of conversion of substrate obtained using a known concentration of the analyte.

35. The method of claim 34, wherein said amino acid is selected from the group consisting of glycine, alanine, valine, leucine, isoleucine, serine, threonine, and methionine.

36. The method of claim 34, wherein said amino acid is leucine or serine.

* * * * *